United States Patent [19]
Rosso

[11] Patent Number: 5,207,234
[45] Date of Patent: May 4, 1993

[54] METHOD FOR MAKING MICRO-ABRASIONS ON HUMAN TISSUE

[75] Inventor: Luciano Rosso, Caselette, Italy

[73] Assignee: L.I.C.A. di Rosso & C.S. n.c., Turin, Italy

[21] Appl. No.: 845,353

[22] Filed: Mar. 5, 1992

Related U.S. Application Data

[60] Continuation of Ser. No. 694,571, May 2, 1991, abandoned, which is a division of Ser. No. 411,452, Sep. 11, 1989, Pat. No. 5,100,412.

[30] Foreign Application Priority Data

Jan. 11, 1988 [IT] Italy .................. 67006 A/88

[51] Int. Cl.$^5$ .............................................. A61B 17/50
[52] U.S. Cl. .................................. 128/898; 606/131; 51/424; 51/425; 51/436
[58] Field of Search ................ 606/131; 604/289, 290; 128/66, 898; 51/424, 425, 436

[56] References Cited

U.S. PATENT DOCUMENTS

| | | |
|---|---|---|
| 1,752,664 | 7/1929 | Forcier . |
| 2,628,456 | 2/1953 | Berg ............................ 51/8 |
| 3,214,869 | 9/1963 | Stryker . |
| 3,286,406 | 11/1966 | Ashworth .................. 51/425 X |
| 3,307,296 | 3/1967 | Ashworth .................. 51/425 X |
| 4,095,378 | 6/1978 | Urakami . |
| 4,395,850 | 8/1983 | Brown ........................ 51/427 |
| 4,433,511 | 2/1984 | Swain ......................... 51/424 |
| 4,488,330 | 12/1984 | Grave . |
| 4,693,756 | 9/1987 | Schlick ....................... 51/322 X |

FOREIGN PATENT DOCUMENTS

| | | |
|---|---|---|
| 1136127 | 5/1957 | France . |
| 2422393 | 1/1978 | France . |
| 1184922 | 10/1987 | Italy ............................ 606/131 |
| 483555 | 5/1938 | United Kingdom . |

*Primary Examiner*—Michael H. Thaler
*Attorney, Agent, or Firm*—Sughrue, Mion, Zinn, Macpeak & Seas

[57] ABSTRACT

A method for making micro-abrasions on human tissue comprising placing a handle having an open chamber therein on human tissue to close said chamber, applying suction to said chamber to sealingly engage the periphery of the chamber with the human tissue and partially sucking the human tissue into said chamber, inducing the flow of air into the chamber by the removal of air from the chamber by suction while restricting entry of ambient air from the surrounding atmosphere into the chamber around the periphery of the chamber, entraining a reducing substance in said flow of air prior to entry of the flow of air into the chamber, directing the reducing substance entering the chamber against the human tissue at an angle less than 90°, entraining used reducing substances and abraded tissue in the flow of air being removed from the chamber by suction and collecting used reducing substances and abraded tissue in a manner to prevent reuse of the reducing substances during continued application of a vacuum to the chamber.

1 Claim, 1 Drawing Sheet

METHOD FOR MAKING MICRO-ABRASIONS ON HUMAN TISSUE

This is a continuation of application Ser. No. 07/694,571 filed May 2, 1991, now abandoned, which is a divisional of application Ser. No. 07/411,452 filed on Sep. 11, 1989, now U.S. Pat. No. 5,100,412.

BACKGROUND OF THE INVENTION

The present invention relates in general to apparatus for making micro-abrasions, particularly for cosmetic and/or therapeutic treatment of human tissue (the removal of scars and stretch marks), as well as for the treatment of hides and similar adherent and non-transpiring materials.

More particularly, the invention is concerned with apparatus of the type including a handle having an inlet passage and an outlet passage which communicate with an aperture intended to be positioned on the surface to be treated, and means for the metered supply of reducing substances in a pneumatic carrier to the aperture of the handle.

SUMMARY OF THE INVENTION

The object of the present invention is to produce apparatus of the type defined above, which is simple and cheap to produce and is very effective in operation.

According to the invention, this object is achieved by virtue of the fact that the means for supplying the reducing substances comprise only a vacuum source connected to the outlet passage of the handle for drawing the reducing substances towards the aperture of the handle through the inlet passage thereof.

The aperture of the handle preferably has a configuration which can be adapted substantially sealingly to the surface to be treated.

According to one preferred embodiment of the invention, the inlet passage of the handle is connected to a supply container for the reducing substances which has in its base a plurality of air-intake apertures with associated regulator valve means, and the outlet passage of the handle is connected to a discharge container which has an outlet aperture connected to a vacuum pump.

Filter means are conveniently associated with the intake apertures of the supply container for achieving a shaking up of the reducing substances by means of a valve and regulating means.

Conveniently, the supply container is provided with electrical means for heating the reducing substances.

BRIEF DESCRIPTION OF THE DRAWINGS

Further characteristics and advantages of the present invention will become clear from the detailed description which follows with reference to the appended drawing, provided by way of non-limiting example which shows apparatus for making micro-abrasions according to the invention, in diagrammatic form.

DETAILED DESCRIPTION OF THE INVENTION

Figure 1:
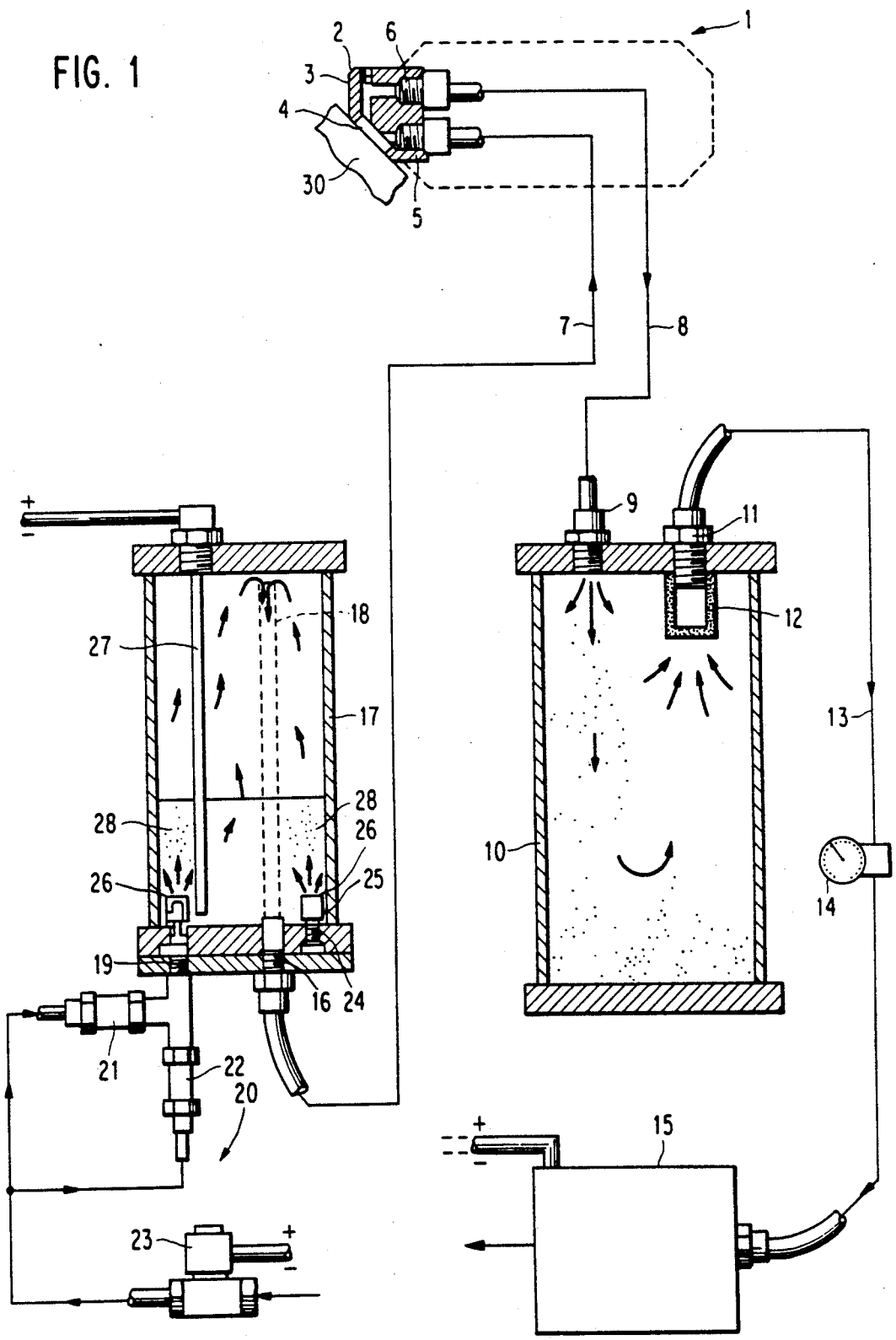

With reference to the drawing, a handle, schematically indicated 1, normally has an anatomically-shaped grip and is provided at one end with an interchangeable head 2 which can assume shapes different from that illustrated, in dependence on the use for which the apparatus is intended. In this instance, the head 2 has an inclined front wall 3 forming an aperture 4 which is adapted to be positioned, in use, on the surface 30 to be treated as shown in the drawing.

The aperture 4 communicates at one side with an inlet passage 5 and at the opposite side with an outlet passage 6, and these are connected to respective tubes 7, 8 connected to the handle 1. The inclination of the wall 3, and hence of the aperture 4, to the inlet passage 5 is of the order of 45°. The inlet passage is oriented substantially perpendicular to the outlet passage.

The tube 8 is connected through an inlet connector 9 to a recovery container 10 having an outlet connector 11 with an associated filter member 12. The outlet connector 11 is connected to an intake tube 13 which is connected to an electric vacuum pump 15 through a vacuum-gauge 14 with a regulator.

The tube 7 is connected to a base connector 16 of a supply container 17 into which a quantity of reducing substances S, normally constituted by abrasive particles of various sizes, is introduced. At rest, the reducing substances S occupy the lower region of the container 17, beneath the mouth of an intake tube 18 which communicates with the base connector 16 and has a hole 28 at its lower end. According to a variant, not illustrated, the intake tube 18 may open outside the container 17.

A passage 19 is situated in the base of the container 17 and communicates with the atmosphere through a valve system, generally indicated 20, including a pair of one-way valves 21, 22 supplied by a solenoid valve 23.

The passage 19 opens into an annular manifold 24 formed in the base of the container 17 and communicating with the interior thereof through a ring of axial holes 25 with associated intake and shaking filters 26.

An electrical resistor 27 is also inserted in the container 17 for heating the reducing substances S.

In use, after the vacuum pump 15 has been activated, the head 2 is applied against the surface to be treated, with the aperture 4 arranged in correspondence with the region on which the micro-abrasions are to be made. The closure of the hole 4 closes the intake circuit and the vacuum generated in the aperture 4 causes the almost hermetic adhesion to the surface to be treated against the edge of the aperture 4. The softer and more resilient the surface, the tighter will be the seal: in the case of human tissue, hermetic adhesion to the edge of the aperture 4 is achieved even with moderate values of the vacuum generated by the vacuum pump 15.

As a result of the vacuum, the reducing substances S held in the container 17 are sucked through the hole 28 together with the air which is drawn through the tube 18, the apertures 25 and the valve unit 20, and reach the aperture 4 under vacuum through the tube 7 and the inlet passage 5. The reducing substances S pass over that region of the surface 30 to be treated which is delimited by the aperture 4, causing micro-abrasions, and reach the container 10 through the outlet connector 6 and the tube 8, being collected therein together with the particles and detritus removed from the surface being treated.

The degree of micro-abrasion caused on the surface under treatment is adjustable by the operation of both the regulator 14 associated with the vacuum pump 15 and the solenoid valve unit 20, whereby the flow of atmospheric air sucked into the container 17 is regulated automatically. Moreover, the air inlet can be closed by means of the valve unit 20 to create a vacuum in the container 17, the readmittance of air through the apertures 25 and the filter 26 effectively shaking up the mass of reducing substances S in the container 17 and thus preventing cavitation.

Naturally, the forms of embodiment and details of construction of the apparatus may be varied widely with respect to those described and illustrated, without thereby departing from the scope of the represent invention.

Thus, for example, the vacuum pump could be replaced by equivalent means adapted to create a vacuum in correspondence with the handle.

I claim:

1. A method for making micro-abrasions on human tissue comprising:

placing a handle having an open chamber thereon on human tissue to close said chamber;

applying suction to said chamber to sealingly engage the periphery of the chamber with the human tissue and to apply a suction force to the human tissue toward said chamber;

inducing the flow of air into the chamber only by the removal of air from the chamber by suction while restricting entry of ambient air from the surrounding atmosphere into the chamber around the periphery of the chamber;

entraining a reducing substance in said flow of air prior to entry of the flow of air into the chamber;

directing substantially all the reducing substance entering the chamber directly against the human tissue at an angle of substantially 45°;

entraining used reducing substances and abraded tissue in the flow of air being removed from the chamber by suction; and collecting used reducing substances and abraded tissue in a manner to prevent reuse of the reducing substances during continued application of a vacuum to the chamber.

* * * * *